United States Patent [19]

Shimizu et al.

[11] Patent Number: 5,208,380

[45] Date of Patent: May 4, 1993

[54] PROCESS FOR PREPARING MONOALLYLAMINE

[75] Inventors: Shinkichi Shimizu, Kawanishi; Takayuki Shoji, Osaka; Hideki Nakao, Sakai, all of Japan

[73] Assignee: Koei Chemical Co., Ltd., Osaka, Japan

[21] Appl. No.: 866,268

[22] Filed: Apr. 13, 1992

Related U.S. Application Data

[63] Continuation of Ser. No. 631,233, Dec. 20, 1990, abandoned.

[30] Foreign Application Priority Data

Dec. 22, 1989 [JP] Japan .................. 1-333066
Nov. 27, 1990 [JP] Japan .................. 2-328191

[51] Int. Cl.$^5$ .................................. C07C 211/21
[52] U.S. Cl. .................... 564/509; 502/302; 502/303; 502/304; 502/349
[58] Field of Search ............. 564/509; 502/302, 303, 502/304, 349

[56] References Cited

U.S. PATENT DOCUMENTS

| | | | |
|---|---|---|---|
| 1,065,160 | 6/1913 | Merling et al. ............ | 564/509 |
| 2,216,548 | 10/1940 | Converse .................... | 260/585 |
| 2,487,832 | 11/1949 | Searle ........................ | 568/630 |
| 3,175,009 | 3/1965 | Koski et al. ................ | 260/585 |
| 4,465,889 | 8/1984 | Anthony et al. ........... | 502/71 |
| 4,611,084 | 9/1986 | Mossman .................... | 568/630 |

FOREIGN PATENT DOCUMENTS

| | | | |
|---|---|---|---|
| 0525752 | 6/1956 | Canada ....................... | 564/509 |
| 320269 | 6/1989 | European Pat. Off. . | |
| 0012685 | 6/1965 | Japan ......................... | 564/509 |
| 63-2958 | 1/1988 | Japan . | |

OTHER PUBLICATIONS

Beilsteins Handbuch der Organischen Chemie, (4th Edition, vol. 4, 1922, pp. 205-206).

*Primary Examiner*—Glennon H. Hollrah
*Assistant Examiner*—Brian M. Burn
*Attorney, Agent, or Firm*—Armstrong, Westerman, Hattori, McLeland & Naughton

[57] ABSTRACT

A process for preparing monoallylamine represented by the formula (II):

$$CH_2=CHCH_2NH_2 \qquad (II)$$

which comprises: catalytically reacting isopropanolamine represented by the formula (I):

$$\underset{CH_3CHCH_2NH_2}{\overset{OH}{|}} \qquad (I)$$

in a gaseous phase in the presence of a catalyst having dehydrating property. According to the preparation process of the present invention, monoallylamine can be easily obtained in high selectivity and high yield.

3 Claims, No Drawings

PROCESS FOR PREPARING MONOALLYLAMINE

This application is a continuation of application Ser. No. 631,233 filed Dec. 20, 1990 now abandoned.

BACKGROUND OF THE INVENTION

The present invention relates to a process for preparing monoallylamine, and more particularly to a process for preparing monoallylamine which is useful as a modifier for polymers, an intermediate of medicine or agricultural chemicals, and the like.

With respect to preparation of monoallylamine, as a general preparation method, there have been known (a) a method wherein an allyl halide is reacted with ammonia which is described in U.S. Pat. Nos. 2,216,548 and U.S. Pat. No. 3,175,009 and (b) a method wherein an allyl alcohol is reacted with ammonia which is described in Japanese Unexamined Patent Publication (Tokkyo Kokai) No. 63-2958 and No. 1-153660.

According to the method (a), however, since a hydrogen halide is produced with the formation of allylamine, the produced allylamine is obtained in the state of a hydrohalogenide of amine. Accordingly, in order to obtain free amine, a recovering step of amine wherein the salt is neutralized with an alkali is required, that is, the preparation operation is complex.

On the other hand, according to the method (b), water is produced as a by-product with the formation of allylamine. Accordingly, the neutralization step required in the method (a) is not necessary. As a catalyst in the method (b), however, a platinum complex is used in the preparation method described in Tokkyo Kokai No. 63-2958 or a palladium complex is used in the preparation method described in Tokkyo Kokai No. 1-153660, whereby the improvement of conversion is attained. Since such an expensive noble metal catalyst is used in homogeneous reaction system, troublesome operation steps for recovering the catalyst are required.

An object of the present invention is to solve the above-mentioned defects, that is, to provide a process for preparing selectively monoallylamine without a complex reaction process.

This and the other objects of the present invention will become apparent from the description hereinafter.

SUMMARY OF THE INVENTION

It has now been found that when isopropanolamine is subjected to gaseous phase catalytic reaction in the presence of a dehydrating catalyst, monoallylamine is selectively produced.

In accordance with the present invention, there is provided a process for preparing monoallylamine represented by the formula (II):

CH$_2$=CHCH$_2$NH$_2$  (II)

which comprises: catalytically reacting isopropanolamine represented by the formula (I):

OH
|
CH$_3$CHCH$_2$NH$_2$  (I)

in a gaseous phase in the presence of a catalyst having dehydrating property.

DETAILED DESCRIPTION

According to the preparation process of the present invention, as mentioned above, dehydration reaction of isopropanolamine represented by the formula (I):

OH
|
CH$_3$CHCH$_2$NH$_2$  (I)

takes place catalytically in a gaseous phase in the presence of the catalyst having dehydrating property to give monoallylamine represented by the formula (II):

CH$_2$=CHCH$_2$NH$_2$  (II)

As the catalyst having dehydrating property in the present invention, there is used zirconium oxide, lanthanum oxide, yttrium oxide, cerium oxide, neodymium oxide, praseodymium oxide, a compound generally used as a dehydrating catalyst in preparation of an olefin from an alkyl alcohol such as activated alumina, niobic acid, montmorillonite, niobium phosphate or titanium oxide, or the like. The catalyst may be used alone or as a mixture thereof. Among them, zirconium oxide, lanthanum oxide, yttrium oxide, cerium oxide, neodymium oxide and praseodymium oxide are particularly preferably used since they are excellent in dehydration reaction efficiency and can selectively produce the desired compound, monoallylamine. Other catalysts than the above-mentioned may be used within a range such that the objects of the present invention are not impaired.

It is preferable that, for instance, an oxide of alkali metal such as lithium, sodium, potassium, rubidium or cesium, an oxide of alkaline earth metal such as barium, magnesium or calcium and/or thallium oxide is admixed as a promoter with the catalyst having dehydrating property. The promoter may be used alone or as a mixture thereof. By the addition of the promoter, the selectivity of monoallylamine is increased. The percentage of the promoter is from 0.01 to 10 % by mole based on the total mole(s) of the catalyst and the promoter, preferably from 0.1 to 3 % by mole. When the percentage of the promoter is less than 0.01 % by mole, the improvement of the selectivity of monoallylamine cannot be obtained. On the other hand, when the percentage is more than 10 % by mole, it tends to lower the conversion of isopropanolamine due to the lowering of the activity of the catalyst.

As the catalyst used in the present invention, both commercially available goods and products made by a known preparation process can be used.

As an example, with respect to zirconium oxide, lanthanum oxide, yttrium oxide, cerium oxide, neodymium oxide or praseodyium oxide, one embodiment of the preparation process of the catalyst is explained as follows:

As a raw material of each of zirconium oxide, lanthanum oxide, yttrium oxide, cerium oxide, neodymium oxide and praseodyium oxide, there is used, for instance, its corresponding nitrate, chloride, carbonate, sulfate, acetate, or the like.

A pH of an aqueous solution containing the raw material of the each oxide as mentioned above is adjusted to a pH of around 7 by using aqueous ammonia. After a produced precipitate is filtered off from the aqueous solution, it is washed with water and then is dried. The dried precipitate is calcined in air at a temperature of 300° to 1000° C., preferably from 400° to 900° C., for 3 to 8 hours to give a desired oxide.

When, as the promoter, the oxide of alkali metal such as lithium, sodium, potassium, rubidium o cesium, an oxide of alkaline earth metal such as barium, magnesium or calcium or thallium oxide is admixed with the catalyst, the promoter can be admixed with the catalyst by a known method such as co-precipitation method, impregnation method or kneading method, using as a raw material of the promoter, the corresponding hydroxide, chloride, nitrate, carbonate or acetate to the desired promoter.

For instance, an aqueous solution of the raw material of the oxide of alkali metal, the oxide of alkaline earth metal or thallium oxide is prepared. The obtained aqueous solution is added to the catalyst of the present invention, preferably at least one oxide selected from the group consisting of zirconium oxide, yttrium oxide, lanthanum oxide, cerium oxide, neodymium oxide and praseodyium oxide, and the mixture is kneaded, dried, and calcined in air at a temperature of 200° to 1000° C., preferably from 300° to 900° C., for 3 to 8 hours to give a catalyst containing the alkali metal oxide, the alkaline earth metal oxide or thallium oxide.

In the present invention, the obtained catalyst can be used as it is. Also, if necessary, the catalyst may be supported on an inert substance used as a carrier of a solid catalyst such as silica, alumina, silica-alumina, silicon carbide (Carborundum) or Celite. In case of using the catalyst supported on the carrier, the catalyst can be supported on the carrier according to a known method such as co-precipitation method, impregnation method, kneading method or coating method.

In the present invention, the shape and size of the catalyst are not particularly limited and are suitably decided depending on the use conditions. For instance, the catalyst can be used in the state of a powder, cylinders, granules, or the like.

In the present invention, the dehydration reaction of isopropanolamine can be conducted by subjecting isopropanolamine to catalytic reaction in gaseous phase in the presence of the catalyst having dehydrating property.

Isopropanolamine used in the present invention may contain a diluent such as nitrogen gas, steam, ammonia gas, or the like. The mixing ratio of the diluent to gaseous isopropanolamine is not particularly limited. The molar ratio of the diluent/gaseous isopropanolamine is adjusted to generally from 0/1 to 50/1, preferably from 0/1 to 10/1.

The contact time of the raw material gas, that is, gaseous isopropanolamine or the mixture of gaseous isopropanolamine and the diluent with the catalyst is not particularly limited and can cover a wide range. It is preferable that the space velocity is from 300 to 8000 $hr^{-1}$, more preferably from 500 to 6000 $hr^{-1}$. When the space velocity is less than 300 $hr^{-1}$, the selectivity of monoallylamine is remarkably lowered. On the other hand, when the space velocity is more than 8000 $hr^{-1}$, it tends to lower the conversion of isopropanolamine.

The reaction temperature is generally from 200° to 700° C., preferably form 300° to 600° C. When the reaction temperature is less than 200° C., the conversion of isopropanolamine is lowered. On the other hand, when the reaction temperature is more than 700° C., it tends to lower the selectivity of monoallylamine.

The catalytic reaction is generally conducted at ordinary pressure (atmospheric pressure), and can be conducted under reduced pressure or under pressure.

Also, the catalytic reaction can be conducted in a fixed bed or a fluidized bed.

The produced as by the catalytic reaction of the raw material gas with the catalyst is cooled and collected as it is, or the cooled gas is absorbed into a suitable solvent such as water and is collected. Then, the collected gas or the solvent containing the gas is subjected to the separation and purification such as distillation to give the desired compound, monoallylamine.

The present invention is more specifically described and explained by means of the following Examples wherein all per cents and parts are by weight unless otherwise noted. It is to be understood that the present invention is not limited to the Examples, and various changes and modifications may be made in the invention without departing from the spirit and scope thereof.

EXAMPLES 1 TO 3

In one liter of water was dissolved 110 g of zirconium nitrate and a 28% aqueous ammonia was added to the aqueous solution of zirconium nitrate to adjust to a pH of 7. The produced precipitate was washed with 3 l of water according to decantation and was filtered off, further it was washed with 2 l of water. Then, the precipitate was dried at 100° C. for 15 hours and was calcined at 800° C. for 5 hours to give zirconium oxide ($ZrO_2$). A glass cylindrical reaction tube (length: 400 mm, inside diameter: 16 mm) was filled with 3 ml of the obtained zirconium oxide ($ZrO_2$). A raw material gas of nitrogen gas and isopropanolamine gas was prepared so as to get a molar ratio of nitrogen gas/isopropanolamine as shown in Table 1. The raw material gas was introduced into the reaction tube at a space velocity shown in Table at a temperature shown in Table 1.

The produced reaction gas was absorbed into water for 10 minutes and the water absorbing monoallylamine was analyzed by gas chromatography. A conversion of isopropanolamine, and a yield and a selectivity of monoallylamine were calculated according to the following formulas:

Conversion (% by mole) =

$$\frac{\text{Amount of reacted isopropanolamine (mole)}}{\text{Amount of supplied isopropanolamine (mole)}} \times 100$$

Yield (% by mole) =

$$\frac{\text{Amount of produced monoallylamine (mole)}}{\text{Amount of supplied isopropanolamine (mole)}} \times 100$$

Selectivity (% by mole) =

$$\frac{\text{Amount of produced monoallylamine (mole)}}{\text{Amount of reacted isopropanolamine (mole)}} \times 100$$

The results are shown in Table 1.

COMPARATIVE EXAMPLE 1

Isopropanolamine was reacted in the same manner as in Example 1 except that a catalyst was not used.

A conversion of isopropanolamine, and a yield and a selectivity of monoallylamine were calculated in the same manner as in Example 1. The results are shown in Table 1.

EXAMPLES 4 TO 12

Monoallylamine was prepared in the same manner as in Example 1 except that a catalyst shown in Table 1 was used under reaction conditions shown in Table 1.

A conversion of isopropanolamine, and a yield and a selectivity of monoallylamine were calculated in the same manner as in Example 1. The results are shown in Table 1.

A catalyst, $CeO_2$ or $La_2O_3$ was prepared as follows:

(a) Preparation of $CeO_2$

In 500 ml of water was dissolved 200 g of cerium nitrate, and a 28 % aqueous ammonia was added to the aqueous solution of cerium nitrate to adjust to a pH of 7.5. After the mixture was stirred at room temperature for 1 hour, the precipitate was filtered off from the reaction mixture and was washed with 5 l of water. After drying the precipitate at 120° C. for 15 hours, it was calcined in air at 550° C. for 5 hours to give cerium oxide ($CeO_2$).

(b) Preparation of $La_2O_3$

The procedure of the preparation of $ZrO_2$ in Example 1 was repeated except that lanthanum nitrate was used instead of zirconium nitrate to give lanthanum oxide ($La_2O_3$).

conversion of isopropanolamine, and a yield and a selectivity of monoallylamine were calculated in the same manner as in Example 1. The results are shown in Table 2.

EXAMPLE 15

The procedure of the preparation of the catalyst in Example 14 was repeated except that a 10 mL aqueous solution containing 0.15 g of sodium hydroxide was used instead of the aqueous solution containing lithium hydroxide to give a catalyst, zirconium oxide containing 0.77 % by mole of sodium oxide.

Monoallylamine was prepared in the same manner as in Example 1 except that the catalyst as obtained above was used under reaction conditions shown in Table 2. A conversion of isopropanolamine, and a yield and a selectivity of monoallylamine were calculated in the same manner as in Example 1. The results are shown in Table 2.

EXAMPLE 16

The procedure of the preparation of the catalyst in Example 14 was repeated except that a 10 ml aqueous solution containing 0.15 g of potassium hydroxide was used instead of the aqueous solution containing lithium

TABLE 1

| Ex. No. | Kind of catalyst | Reaction conditions | | | | | |
|---|---|---|---|---|---|---|---|
| | | Reaction temperature (°C.) | Space velocity of raw material gas ($hr^{-1}$) | $N_2$/IPOA (molar ratio) | Conversion (% by mole) | Yield (% by mole) | Selectivity (% by mole) |
| 1 | $ZrO_2$ | 420 | 2200 | 2/1 | 97 | 74 | 76 |
| 2 | $ZrO_2$ | 420 | 3800 | 2/1 | 67 | 56 | 84 |
| 3 | $ZrO_2$ | 410 | 1300 | 0/1 | 46 | 43 | 93 |
| 4 | $Y_2O_3$* | 430 | 1900 | 2/1 | 67 | 36 | 52 |
| 5 | $La_2O_3$ | 400 | 1800 | 2/1 | 80 | 43 | 54 |
| 6 | $CeO_2$ | 400 | 2200 | 2/1 | 27 | 16 | 59 |
| 7 | $Nd_2O_3$* | 440 | 1900 | 2/1 | 71 | 42 | 59 |
| 8 | $Pr_6O_{11}$* | 440 | 1700 | 2/1 | 48 | 29 | 60 |
| 9 | $ZrO_2$ (95% by mole) + CoO (5% by mole) | 380 | 1800 | 2/1 | 79 | 61 | 77 |
| 10 | $ZrO_2$ (95% by mole) + $Al_2O_3$ (5% by mole) | 380 | 1900 | 2/1 | 71 | 56 | 79 |
| 11 | $TiO_2$* | 400 | 600 | 0/1 | 48 | 7 | 15 |
| 12 | Activated $Al_2O_3$* | 410 | 1800 | 2/1 | 58 | 7 | 12 |
| Co. Ex. 1 | None | 420 | 2200 | 2/1 | 18 | 0 | 0 |

(Notes)
IPOA: Isopropanolamino
*A commercially available oxide was used.

EXAMPLE 13

Monoallylamine was prepared in the same manner as in Example 1 except that a commercially available zirconium oxide was used under reaction conditions shown in Table 2. A conversion of isopropanolamine, and a yield and a selectivity of monoallylamine were calculated in the same manner as in Example 1. The results are shown in Table 2.

EXAMPLE 14

To 30 g of the same zirconium oxide as used in Example 13 was added a 10 ml aqueous solution containing 0.06 g of lithium hydroxide, and the mixture was admixed in a mortar while further adding water in a suitable amount to the mortar. The obtained mixture was dried at 120° C. for 15 hours, then was calcined in air at 500° C. for hours to give a catalyst, zirconium oxide containing 0.51 % by mole of lithium oxide.

Monoallylamine was prepared in the same manner as in Example 1 except that the catalyst as obtained above was used under reaction conditions shown in Table 2. A hydroxide to give a catalyst, zirconium oxide containing 0.55 % by mole of potassium oxide.

Monoallylamine was prepared in the same manner as in Example 1 expect that the catalyst as obtained above was used under reaction conditions shown in Table 2. A conversion of isopropanolamine, and a yield and a selectivity of monoallylamine were calculated in the same manner as in Example 1. The results are shown in Table 2.

EXAMPLE 17

The procedure of the preparation of the catalyst in Example 14 was repeated except that a 10 ml aqueous solution containing 0.24 g of rubidium hydroxide was used instead of the aqueous solution containing lithium hydroxide to give a catalyst, zirconium oxide containing 0.48 % by mole of rubidium oxide.

Monoallylamine was prepared in the same manner as in Example 1 expect that the catalyst as obtained above was used under reaction conditions shown in Table 2. A conversion of isopropanolamine, and a yield and a selectivity of monoallylamine were calculated in the same manner as in Example 1. The results are shown in Table 2.

EXAMPLE 18

The procedure of the preparation of the catalyst in Example 14 was repeated except that a 10 ml aqueous solution containing 0.15 g of cesium hydroxide was used instead of the aqueous solution containing lithium hydroxide to give a catalyst, zirconium oxide containing 0.21 % by mole of cesium oxide.

Monoallylamine was prepared in the same manner as in Example 1 expect that the catalyst as obtained above was used under reaction conditions shown in Table 2. A conversion of isopropanolamine, and a yield and a selectivity of monoallylamine were calculated in the same manner as in Example 1. The results are shown in Table 2.

EXAMPLE 21

The procedure of the preparation of the catalyst in Example 14 was repeated except that a 10 ml aqueous solution containing 0.71 g of thallium nitrate was used instead of the aqueous solution containing lithium hydroxide to give a catalyst, zirconium oxide containing 0.55 % by mole of thallium oxide.

Monoallylamine was prepared in the same manner as in Example 1 except that the catalyst as obtained above was used under reaction conditions shown in Table 2. A conversion of isopropanolamine, and a yield and a selectivity of monoallylamine were calculated in the same manner as in Example 1. The results are shown in Table 2.

TABLE 2

| Ex. No. | Kind of catalyst | Reaction conditions | | $N_2$/IPOA (molar ratio) | Conversion (% by mole) | Yield (% by mole) | Selectivity (% by mole) |
|---|---|---|---|---|---|---|---|
| | | Reaction temperature (°C.) | Space velocity of raw material gas (hr$^{-1}$) | | | | |
| 13 | $ZrO_2$ | 400 | 2000 | 2/1 | 98 | 63 | 64 |
| 14 | $ZrO_2$ (99.49% by mole) + $Li_2O$ (0.51% by mole) | 400 | 2000 | 2/1 | 91 | 68 | 75 |
| 15 | $ZrO_2$ (99.23% by mole) + $Na_2O$ (0.77% by mole) | 400 | 1800 | 2/1 | 92 | 68 | 74 |
| 16 | $ZrO_2$ (99.45% by mole) + $K_2O$ (0.55% by mole) | 400 | 1800 | 2/1 | 98 | 80 | 82 |
| 17 | $ZrO_2$ (99.52% by mole) + $Rb_2O$ (0.48% by mole) | 400 | 1800 | 2/1 | 95 | 75 | 79 |
| 18 | $ZrO_2$ (99.79% by mole) + $Cs_2O$ (0.21% by mole) | 400 | 1800 | 2/1 | 92 | 68 | 72 |
| 19 | $ZrO_2$ (98.5% by mole) + $MgO$ (1.5% by mole) | 400 | 1800 | 2/1 | 94 | 74 | 79 |
| 20 | $ZrO_2$ (99.17% by mole) + $CaO$ (0.83% by mole) | 400 | 1800 | 2/1 | 99 | 73 | 74 |
| 21 | $ZrO_2$ (99.45% by mole) + $Tl_2O$ (0.55% by mole) | 400 | 1800 | 2/1 | 95 | 68 | 72 |

(Note)
IPOA: Isopropanol amino

EXAMPLE 19

The procedure of the preparation of the catalyst in Example 14 was repeated except that a 10 ml aqueous solution containing 0.94 g of magnesium nitrate [$Mg(NO_3)_2.6H_2O$] was used instead of the aqueous solution containing lithium hydroxide to give a catalyst, zirconium oxide containing 1.5 % by mole of magnesium oxide.

Monoallylamine was prepared in the same manner as in Example 1 expect that the catalyst as obtained above was used under reaction conditions shown in Table 2. A conversion of isopropanolamine, and a yield and a selectivity of monoallylamine were calculated in the same manner as in Example 1. The results are shown in Table 2.

Example 20

The procedure of the preparation of the catalyst in Example 14 was repeated except that a 10 ml aqueous solution containing 0.15 g of calcium hydroxide was used instead of the aqueous solution containing lithium hydroxide to give a catalyst, zirconium oxide containing 0.83 % by mole of calcium oxide.

Monoallylamine was prepared in the same manner as in Example 1 expect that the catalyst as obtained above was used under reaction conditions shown in Table 2. A conversion of isopropanolamine, and a yield and a selectivity of monoallylamine were calculated in the same manner as in Example 1. The results are shown in Table 2.

As apparent from the results shown in Table 1 and Table 2, it would be recognized that according to the preparation process of the present invention, the desired compound of the present invention, monoallylamine can be preferably obtained.

Particularly, it would be recognized that when using zirconium oxide, yttrium oxide, lanthanum oxide, cerium oxide, neodymium oxide and praseodymium oxide as the catalyst, especially when using zirconium oxide, monoallylamine can be obtained in high selectivity and high yield.

Also, by admixing the oxide of alkali metal and/or the oxide of alkaline earth metal with the catalyst, the selectivity and the yield of monoallylamine can be further improved.

In each Example 1–20, whether propylene imine was produced as a by-product was checked by gas chromatograph. As results, it was confirmed that propylene imine was not produced in all Examples.

According to the preparation process of the present invention, monoallylamine can be easily and selectively obtained from isopropanolamine. Accordingly, the preparation process of the present invention is excellent as the industrial preparation process of monoallylamine.

In addition to the ingredients used in the Examples, other ingredients can be used in the Examples as set forth in the specification to obtain substantially the same results.

What we claim is:

1. A process for preparing monoallylamine represented by the formula (II):

$$CH_2=CHCH_2NH_2 \quad (II)$$

which comprises: catalytically reacting isopropanolamine represented by the formula (I):

$$\underset{CH_3CHCH_2NH_2}{\overset{OH}{|}} \quad (I)$$

in a gaseous phase in the presence of a catalyst comprising at least one oxide selected from the group consisting of zirconium oxide, lanthanum oxide, yttrium oxide, cerium oxide, neodymium oxide and praseodymium oxide.

2. The process of claim 1, wherein said catalyst contains a promoter comprising at least one oxide selected from the group consisting of oxides of alkali metals, oxides of alkaline earth metals and thallium oxide.

3. The process of claim 2, wherein said catalyst is zirconium oxide.

* * * * *